United States Patent [19]

LaCourse

[11] Patent Number: 4,572,199
[45] Date of Patent: Feb. 25, 1986

[54] SYSTEM TO DETERMINE ARTERIAL OCCLUSION AND OTHER MALADIES

[75] Inventor: John R. LaCourse, Lee, N.H.

[73] Assignee: University of New Hampshire, Durham, N.H.

[21] Appl. No.: 677,315

[22] Filed: Nov. 30, 1984

Related U.S. Application Data

[63] Continuation of Ser. No. 453,605, Dec. 27, 1982, abandoned.

[51] Int. Cl.$^4$ ............................................. A61B 10/00
[52] U.S. Cl. ................................. 128/657; 128/670; 128/688
[58] Field of Search ............... 128/657, 691, 745, 793, 128/733, 687, 688, 689, 670, 700

[56] References Cited

U.S. PATENT DOCUMENTS

| | | | |
|---|---|---|---|
| 3,734,086 | 5/1973 | Phelps, Sr. ........................... | 128/687 |
| 3,948,248 | 4/1976 | Zuckerman et al. ............... | 128/660 |
| 4,165,736 | 8/1979 | Wolfson .............................. | 128/687 |
| 4,213,464 | 7/1980 | Katz et al. ........................... | 128/745 |
| 4,378,813 | 4/1983 | Feldstein et al. .................... | 128/774 |

OTHER PUBLICATIONS

Bynke et al., "A Handy Instrument . . . Results", Ophthalmologica 148: 1964.
Rasmussen et al., "Communications . . . ", IEEE 1981.
Best et al., "Techniques of Ocular Pulse Analysis . . . ", Arch. Opth. 7/1974.
Horven et al., "Crest Time Evaluation . . . ", Arch. Opth. 7/1971.
Best et al., "Graphic Analysis . . . ", Arch. Opth. 3/1971.
Bynke, "Screening Diagnosis of Carotid Occlusion . . . ", Neurology 4/1976.
Sand et al., "Ophthalmic Arterial Blood Pressure . . . ", Jul. 1975.
Fields et al., "Joint Study . . . ", 3/1968.
Digilab-Specifications 7/1979.
Galin et al., "The Ocular Pulse", Opth. & Otol. 1972.
Walden et al., "Complimentary Methods . . . ", Surgery 1980.

Primary Examiner—Edward M. Coven
Attorney, Agent, or Firm—Robert Shaw

[57] ABSTRACT

A system for noninvasively sensing ocular pulses of a mammal, which pulses serve as a basis for indicating presence of a disease or malfunctioning body part such as, for example, a condition of arterial occlusion. The system employs piezoelectric transducers to sense the ocular pulses which are analyzed, also, in the case of arterial occlusion with simultaneously obtained ECG signals.

32 Claims, 6 Drawing Figures

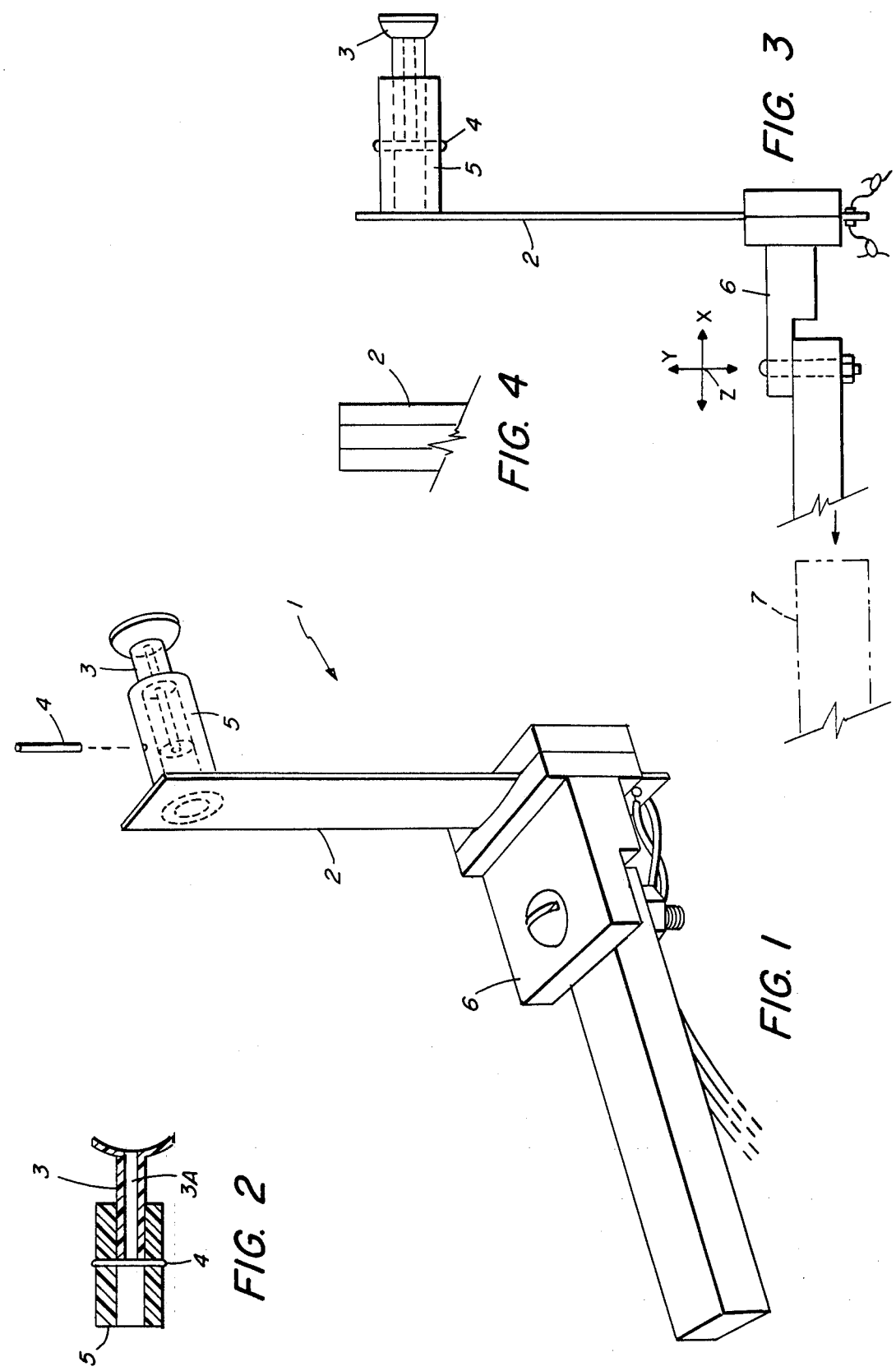

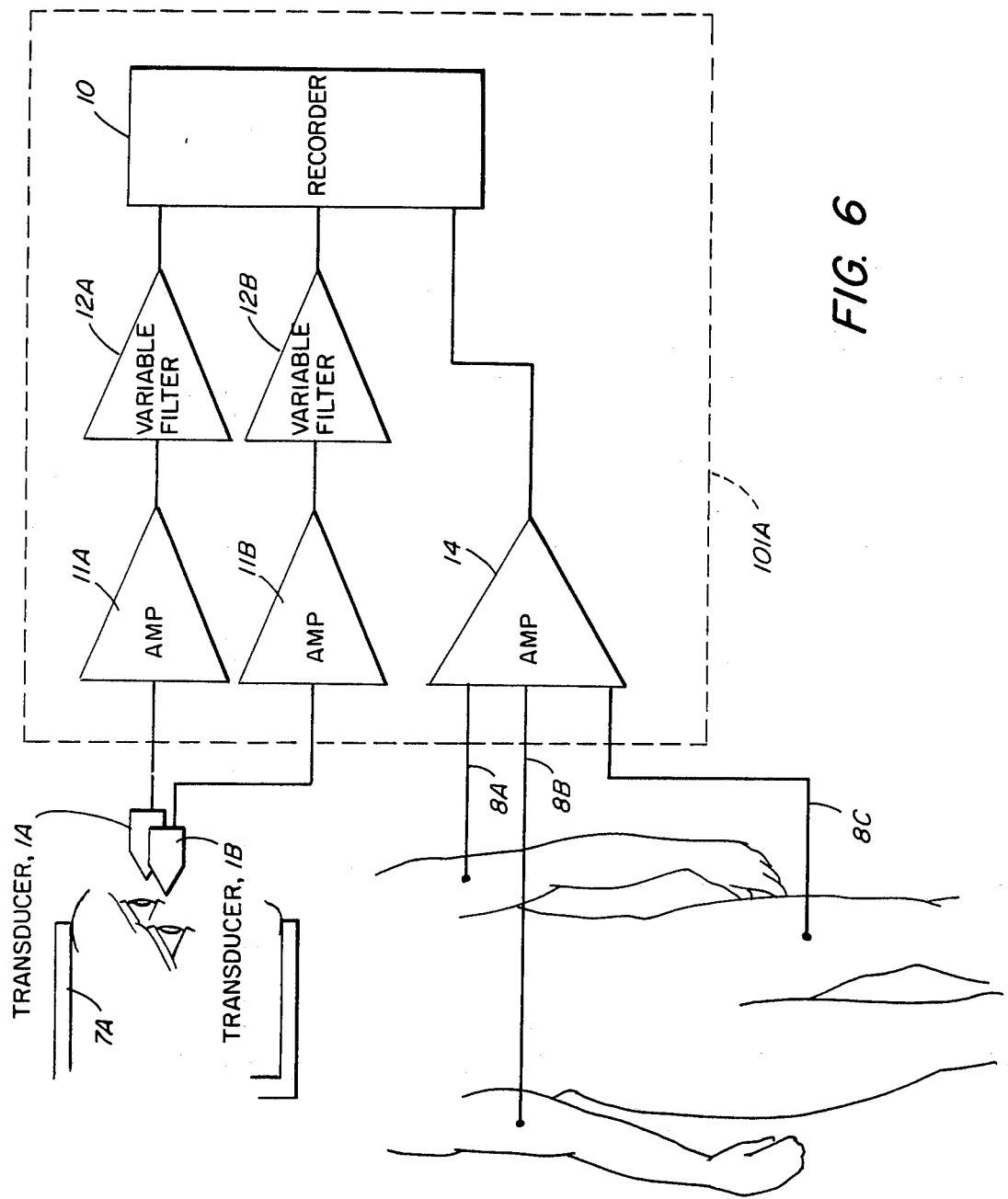

SYSTEM TO DETERMINE ARTERIAL OCCLUSION AND OTHER MALADIES

This is a continuation application of Ser. No. 453,605, filed Dec. 27, 1982, now abandoned.

The present invention relates to systems and methods to determine arterial occlusion and glaucoma.

By way of general background, attention is called to "Joint Study of Extracranial Arterial Occlusion. II. Arteriography Techniques, Sites and Complications," *J. A. M. A.* 203:961, Hass et al., (1968) and "Measurement of Internal Carotid Artery Blood Volume Pulsations by Noncontact Ocular Photoelectric Plethysmography." *IEEE TRANS.* Biomed. Eng., BME-28(8) 573, Rasmussen et al. (1981).

Stroke accounts for the death or disability of nearly one-half million people each year in this country and it is estimated that as many as 30 percent of these strokes are the result of stenosis or occlusion of the extracranial arteries. If this narrowing in these arteries can be detected before any permanent brain damage occurs, it usually can be surgically corrected.

Currently carotid angiography is usually employed to investigate stenosis or occlusion in the extracranial arteries. Carotid angiography is an invasive procedure wherein a catheter is inserted into the artery in situ. Although the carotid angiography procedure is the best way of demonstrating the site of an occlusive lesion, it does incur appreciable morbidity and mortality. Consequently, angiography is often not applicable for the early detection and periodic evaluation of many patients with suspected carotid occlusive disease. Therefore, there is a need for a safe, simple, and reliable diagnostic screening procedure for the noninvasive evaluation of carotid occlusive disease. During the past few years there have been many noninvasive screening tests developed for carotid occlusive disease, but no single procedure has yet emerged at preeminent. The present disclosure describes a new system to measure the ocular pulse (OP) in humans and in other mammals and to diagnose carotid insufficiency and, in some instances, glaucoma therefrom.

The OP is the minute, radial displacement of the corneal surface of the eye caused by arterial pressure pulsations in the ocular circulation acting on the compliance of the cornea. Features of the OP waveform (i.e., shape, amplitude, duration) have been shown by several workers (Best and Rogers, "Techniques of Ocular Pulse Analysis in Carotid Stenosis," *Arch. Opthalmol.* 92:54 (1974); Horven and Nornes, "Crest Time Evaluation of Corneal Indentation Pulse," *Arch. Opthalmol.* 86:5 (1971) to be important diagnostic indicators of cerebrovascular disease (CVD) in which the common carotid and/or lower internal carotid arteries are significantly occluded. To be more exact, with each heartbeat blood vessels supplying the eye cause a pressure wave or pulse to propagate to the cornea, producing a slight distension (1 to 50 micrometers).

Alterations in the ocular blood supply are reflected in parameters defining the ocular pulse. Differences in ocular pulses in both eyes are associated with pathology (Best et al., "Graphic Analysis of the Ocular Pulse in Carotid Stenosis," *Arch. Opthalmol.* 85:315 (1971); Bynke, H., "Screening Diagnosis of Carotid Occlusion by Means of Oculosphygmography," *Neurology* 16:383 (1966); Sand et al., "Ophthalmic Arterial Blood Pressures Measured by Ocular Pneumoplethysmography," *Arch. Surg.* 110:813 (1975); and Galin et al., "The Ocular Pulse," *Trans. Am. Acad. Ophth. & Otol.* 76:1535 (1972)). By the monitoring of the ocular pulse, that class of vascular occlusive diseases causing alterations in ocular the pulse become amenable to rapid early detection.

Accordingly, it is a principal object of the present invention to provide a simple and reliable diagnostic screening system for noninvasive evaluation of carotid occlusive disease.

Another object is to provide a system suitable to sense ocular pulses (OP) and operable to relate those pulses to a condition of carotid occlusive disease.

Still another object is to provide a system of more general use.

A secondary object of the present invention is to provide a simple and reliable diagnostic screening system for noninvasive evaluation of glaucoma.

Another object is to provide a simple and reliable diagnostic screening system for noninvasive evaluation of choroidal melanoma, carotid obstruction, giant cell arteritis, and carotid cavernous sinus fistula.

These and still further objects are addressed hereinafter.

The foregoing objects are achieved, in one aspect of the present invention, in a mechanism to achieve noninvasive measurement of ocular pulses in a mammal, which pulses serve as a basis for determination of any stenosis or occlusion of extracranial arteries of the mammal. The mechanism includes first piezoelectric transducer means to receive ocular pulses from one eye of the mammal and operable to convert the ocular pulses to a first signal of similar electric pulses; second piezoelectric transducer means to receive ocular pulses from the other eye of the mammal and operable to convert the ocular pulses to a second signal of similar electric pulses; ECG means to record heartbeats (i.e., the electrical activity of the heart) of the mammal in the form of electric signals; and display means connected to receive the first signal of similar electric pulses, the second signal of similar electric pulses, and the electric signal and operable to display the same simultaneously as a series of waveshapes to permit observation and comparison of one or more the amplitude of a waveshape derived from said one eye with a waveshape derived from the said other eye, the area under the waveshape from each eye, the amount of distortion of the waveshape derived from each eye, and the delay of each waveshape from each eye with respect to the corresponding ECG signal to permit an inference of any stenosis or occlusion of the extracranial arteries of the mammal being checked therefor. Other mechanisms are discussed, that perform other functions.

The invention is hereafter described with reference to the accompanying drawing in which:

FIG. 1 is an enlarged ($\approx$ two to one) isometric view showing mechanical portions, including a piezoelectric bender, of a part of a system according to the present teachings and includes conductors for connection to electrical circuitry thereof;

FIG. 2 is a sectional elevation view of a portion of the structure in FIG. 1;

FIG. 3 is a side view of most of the mechanical portion in FIG. 1;

FIG. 4 shows, greatly enlarged, a side view of a portion of the piezoelectric bender of FIGS. 1 and 3;

FIG. 6 shows diagrammatically a system of the type shown in FIG. 5 in conjunction with a patient.

Figure 5:
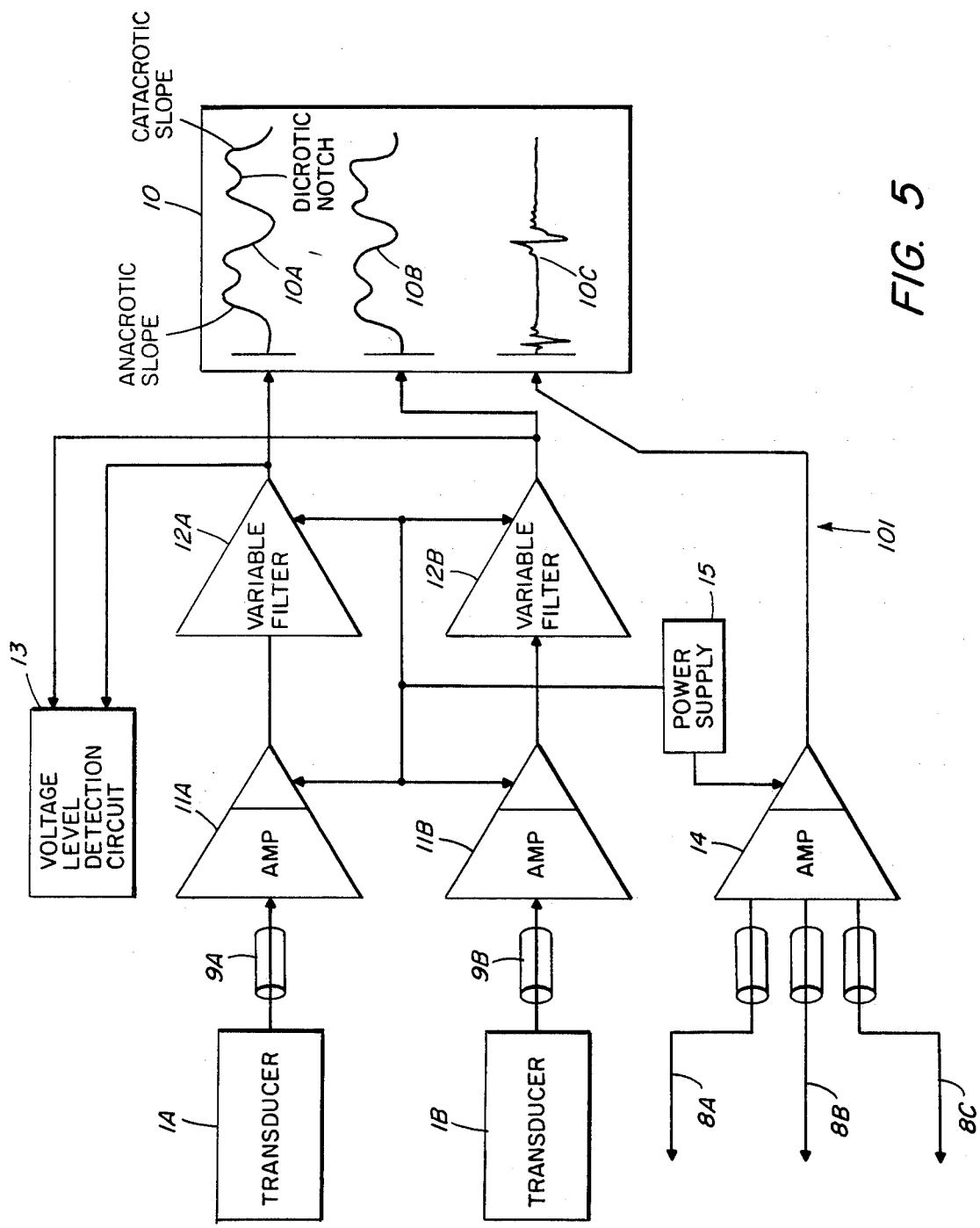
FIG. 5 shows diagrammatically a system that includes both mechanical and electrical elements of a system employing the present concepts.

Turning now to the figures, the mechanism (or system) labeled 101 in FIG. 5, called Piezoelectric Ocular Pulse Measurement System (POPMS) by the present inventor, serves as a basis for determination of an occlusion of extracranial arteries of a mammal. The POPMS diagnostic mechanism, as is discussed in detail hereinafter, permits quick, noninvasive evaluation of the physical condition of the carotid artery. While emphasis herein is use of the general concepts in connection discovery of occlusion of extracranial arteries of the mammal, it is noted that the invention is broader in scope.

By way of brief introduction, the diagnostic system 101 senses ocular pulses of both the left eye and the right eye of the mammal while, at the same time, recording heartbeats (i.e., the electrical activity of the heart, ECG) of the mammal. All three pulses are converted to electric signals which are simultaneously displayed and/or stored by a device 10 which may be, for example, a strip chart recorder, an oscilloscope or a magnetic tape recorder or a combination thereof. The labels 10A, 10B and 10C in FIG. 5 designate respectively a series of waveshapes of a first signal of similar electric pulses derived from the left eye of the mammal, a second signal of similar electric pulses derived from the right eye of the mammal and ECG electric signals recording the heartbeat of the mammal.

The waveshapes of the signals 10A, 10B and 10C serve as a basis for analysis according to the present teaching. For example, a trained operator viewing the waveshapes 10A, 10B and 10C can compare the amplitude of the waveshape derived from the left eye with the amplitude of the waveshape derived from the right eye, the areas under the waveshapes, and the delay of each waveshape from each eye with respect to the corresponding ECG signal to permit an interference of any stenosis or occlusion of the extracranial arteries of the mammal being checked therefor.

It has been shown by Galin et al (1972) and Best et al. (1971) and others that the degree of reduction in the ocular pulse amplitude is related directly to the amount of carotid stenosis. Also, it has been shown by the above scientists that acute common carotid ligation caused a marked reduction in the amplitude of the homolateral ocular pulse, disappearance of the dicrotic notch, delay in crest time, and reduction in the steepness of the anacrotic and catacrotic slopes. In other words, the degree of variation in the amplitude, shape, and/or area under the waveform between left and right ocular pulse waveforms denote the extent of the stenosis. Walden et al., "Complementary Methods for Evaluating Carotid Stenosis: A Biophysical Basis for Ocular Pulse Wave Delays," *Surgery* 88(1):162 (1980), has demonstrated that the degree of delay from the ECG signal to the ocular pulse waveform indicates the degree of compliance distal to the stenosis, i.e., the physical condition of the artery. In all comparison of the characteristics of the left to right ocular pulse waveforms and comparison of both waveforms to an ECG signal, provides information to the degree of stenosis and to the physical condition of the occluded artery.

The system 101 includes a first transducer assembly 1A to receive ocular pulses from the left eye of the mammal and operable to convert the ocular pulses to a first signal of similar electric pulses (e.g., the signal represented by the trace 10A); a second transducer assembly 1B to receive ocular pulses from the right eye and operable to convert the ocular pulses to a second signal of similar electric pulses (e.g., the signal represented by the trace 10B); and ECG leads 8A, 8B and 8C to record heartbeats of the mammal as represented by the trace 10C. A most important aspect of the present invention is the two devices in the assemblies 1A and 1B, which are piezoelectric devices of the type shown at 1 in FIG. 1 and now discussed.

The device 1 uses a piezoelectric bender or transducer 2 which effects physical contact with the cornea of the eye by way of a presterilized disposable contact lens retriever 3 that has an axial hole 3A in FIG. 2 to prevent a vacuum. The piezoelectric bender 2 is a piezoceramic crystalline bender which is a low power electromechanical transducer capable of converting mechanical energy to electrical energy. The lens retriever 3 is replaceably held within a sleeve 5, stopped by a pin 4 which permits facile replacement of the retriever 3 and maintains calibration after use. Ocular pulses from the eye are thereby transmitted to the piezoceramic (or other) bender 2 which converts the mechanical pulse to electric signals of the type represented by the traces 10A and 10B. The piezoceramic bender actually used is a Gulton, Piezoceramic bender element (R 205S) marketed by Piezo Products Division, Gulton Industries, Inc., 212 Durham Avenue, Metuchen, N. J. 08840, which is a sandwich structure (see FIG. 4) which measures 2 inches in length, 0.5 inches in width and 0.02 inches in thickness.

The disposable retriever 3, as above noted, is held within the Teflon sleeve 5, the sleeve being attached by epoxy cement to the bender 2 which is secured to a base 6 in FIG. 1 and thence to a micromanipulator shown diagrammatically at 7 in FIG. 3. The micromanipulator 7, a trade device, allows placement of the transducer assemblies 1A and 1B, onto the corneal surfaces of the eyes. The manipulator allows movement of the transducer assemblies in three directions (x, y and z) in FIG. 3.

The procedure for obtaining the traces 10A, 10B and 10C is straightforward. For human OP recording, the patient is seated with the head immobilized on a headrest 7A (see FIG. 6) which is attached to the manipulator 7. The ECG leads 8A, 8B and 8C in FIGS. 5 and 6 are placed in the known way. The patient holds both eyelids open while each lens retriever 3 is placed in contact with an eye. The transducers are left in contact with each eye for about three seconds and then retrieved; an ECG of the patient is taken at the same time. The session is over. The retrievers are removed and replaced by new sterilized elements. Synthetic tears may be used to overcome any dryness at the corneal surface; a topical corneal anesthetic may be used.

Returning to FIG. 5, the electrical portions of the system 101 includes coaxial cables 9A and 9B connected as inputs to the first and second isolation amplifiers 11A and 11B to receive respectively a first signal from the first transducer and a second signal from the second transducer. Each of the amplifiers produces variable gain upon the input signal but each serves as well to insulate the patient against leakage currents and amplifier fault currents, a function which is complemented by the Teflon sleeve 5 and the plastic retriever 3. First and second variable filters 12A and 12B receive the amplified signals and supply outputs to provide the traces 10A and 10B. A voltage level detection circuit 13 serves to indicate to the operator when the transducer is in contact with the eye and allows calibration of the system when needed.

The ECG input signals are amplified at 14 (another isolation amplifier), and filtered. A modular power supply 15 furnishes electric power to the various electrical elements just discussed.

The system 101A in FIG. 6 is similar to the system 101. The further figure is used mostly to show a patient in place on the headrest 7A.

The systems 101 and 101A provide reliable and accurate mechanisms for recording mass screening to determine occlusions of extracranial arteries, but either can be used, with slight modification, to sense glaucoma. Glaucoma is one of the most common causes of blindness. It is a disease of the eye in which the intraocular pressure becomes pathologically high, sometimes rising to as high as 70 millimeters of mercury. The average normal intraocular pressure is approximately 16 millimeters of mercury, with a range from 12 to 20. By determining the intraocular pressure, glaucoma can be diagnosed. The new measurement system disclosed herein with slight modification will measure intraocular pressure. It is the beauty of the piezoceramic transducer in that it bends/displaces to force. Therefore, when the transducer is in contact with the eye, a known small amount of displacement is applied to the transducer via the micromanipulator, causing the central portion of the cornea to be displaced inwardly. The amount of displacement of the cornea is directly related to the pressure inside the eye into the cornea, i.e., the intraocular pressure. The displacement of the piezoelectric crystal or the intraocular pressure is given by the crystal as a voltage. With high intraocular pressue, i.e., glaucoma, the cornea will not be displaced inwardly as much as compared to the displacement with normal intraocular pressure; thus when a patient tested suffers from glaucoma a lower voltage will appear at the crystal output as compared to a nonglaucomic state. The method is noninvasive and the likelihood of infection and transmitted disease is greatly reduced.

Further modifications of the invention herein disclosed will occur to persons skilled in the art and all such modifications are deemed to be within the scope of the invention as defined by the appended claims.

What is claimed is:

1. Apparatus to achieve noninvasive measurement of ocular pulses in mammals, which pulses serve as a basis for determination of any occlusion of extracranial arteries of the mammal, comprising:
    a. first piezoelectric transducer means to receive ocular pulses from one eye of the mammal and operable to convert the ocular pulses to a first signal of similar electric pulses,
    b. second piezoelectric transducer means to receive ocular pulses from the other eye of the mammal and operable to convert the ocular pulses to a second signal of similar electric pulses,
    said transducer means comprising a pair of simultaneously operative piezoelectric benders disposed to bend by substantially horizontal movement, having eye contact means positioned to engage simultaneously the corneas of the two eyes disposed substantially vertically and having support means supporting said piezoelectric benders for movement of said eye contact means substantially horizontally into engagement with said corneas,
    c. ECG transducer means to record heartbeats of the mammal in the form of electric signals, and
    d. display means connected to receive the first signal of similar electric pulses, the second signal of similar electric pulses, and the electric signals, and operable to display the same as a series of waveshapes to permit simultaneous observation and simultaneous comparison of the amplitudes and areas of a waveshape derived from each eye, the amount of distortion of the waveshape derived from each eye, and the delay of the waveshape from each eye with respect to the corresponding ECG signal, to permit an inference of any occlusion of the extracranial arteries of the mammal being checked therefor.

2. Apparatus as claimed in claim 1, wherein the support means comprises a pair of three-dimensional micromanipulators.

3. Apparatus as claimed in claim 1, wherein the piezoelectric transducer means are also operative to produce signals corresponding to the intraocular pulse in both eyes simultaneously.

4. Apparatus according to claim 1, wherein the eye contact means is a material which is sufficiently insulating so as to protect the mammal wearing the eye contact means from electrical shock hazard.

5. Apparatus according to claim 4, wherein the material for the eye contact means is rubber.

6. Apparatus according to claim 4, wherein the eye contact means is replaceably held within a plastic sleeve.

7. Apparatus according to claim 6, wherein the eye contact means is a contact lens retriever.

8. Apparatus according to claim 7, wherein the contact lens retriever is presterilized before making contact with the surface of the eye.

9. Apparatus according to claim 8, wherein the contact lens retriever is disposable after each use so as to minimize the likelihood of infection and transmitted diseases to the wearer of the eye contact means.

10. Apparatus according to claim 1, the eye contact means having an aperture, the aperture extending from the surface of the eye contact means making contact with the eye to at least one other surface of the eye contact means, to allow easy, rapid, and safe removal of the eye contact means from the surface of the eye.

11. Apparatus according to claim 1, wherein each eye contact means is attached to its piezoelectric bender by a sleeve to permit the eye contact means to be easily and rapidly installed and replaced and maintain calibration after use.

12. Apparatus according to claim 11, wherein the material for the sleeve attaching the eye contact means to the piezoelectric bender is plastic.

13. Apparatus according to claim 11, wherein the material for the sleeve is Teflon.

14. Apparatus according claim 11, wherein the eye contact means is formed of rubber.

15. Apparatus according to claim 1, wherein the display means comprises:
    a. a first isolation amplifier which produces a first variable gain for the first signal of similar electric pulses received from the first piezoelectric transducer means, and which serves to insulate the mammal wearing the eye contact means from electric shock hazards by leakage currents,
    b. a second isolation amplifier which produces a second variable gain for the second signal of similar electric pulses received from the second piezoelectric transducer means, and which serves to insulate the mammal wearing the eye contact means from electric shock hazards, c. a first variable filter which provides a first waveshaped signal for the first variable gain received from the first isolation amplifier, d. a second variable filter which provides a second waveshaped signal for the second variable gain received from the second isolation amplifier, and e. a readout device which receives the first waveshaped signal from the first variable filter, the second waveshaped signal from the second variable filter, and the electric signal from the ECG transducer, and operable to display the same as a series of waveshapes to permit simultaneous observations and simultaneous comparisons of the amplitudes and the areas of waveshapes derived from each eye, the amount of distortion of the waveshape derived from each eye, and the delay of the waveshape of the ECG signal, to permit an inference of any stenosis or occlusion of the extracranial arteries of the mammal being checked therefor.

16. Apparatus as claimed in claim 15, wherein the readout device is a strip chart recorder.

17. Apparatus as claimed in claim 15, wherein the readout devise is an oscilloscope.

18. Apparatus as claimed in claim 15, wherein the readout device is a magnetic tape recorder.

19. Apparatus as claimed in claim 15, wherein the readout device is a magnetic disk.

20. A noninvasive method of measuring the ocular pulses in mammals, which pulses serve as a basis for determination of any stenosis or occlusion in extracranial arteries of the mammal, comprising:

a. immobilizing the head of the mammal with the corneas of the eyes of the mammal oriented substantially vertically, b. attaching an ECG lead to at least three limbs of the mammal, to record heartbeats of the mammal in the form of electric signals, c. providing a pair of simultaneously operative piezoelectric benders disposed to bend by substantially horizontal movement and having eye contact devices positioned to engage said corneas, respectively, for converting ocular pulses to first and second signals of similar electric pulses, respectively, d. moving said eye contact devices substantially horizontally into engagement with the corneas, respectively, e. displaying waveshapes of the electric ECG signal, the first signal of similar electric pulses, and the second signal of similar electric pulses, and f. comparing the series of waveshapes to permit simultaneous observation and simultaneous comparison of simultaneous observation and simultaneous comparison of characteristics of the waveshapes derived from each eye and the ECG to permit an inference of any stenosis or occlusion of the extracranial arteries of the mammal being examined therefor.

21. A method as claimed in claim 3, further comprising employing said piezoelectric benders to produce electric signals corresponding to the intraocular pulse in both eyes simultaneously.

22. A method as claimed in claim 20, wherein the ECG leads are attached to three limbs of the mammal.

23. A method as claimed in claim 22, wherein the three limbs to which the ECG leads are attached are the left arm, the left leg, and the right arm.

24. A method as claimed in claim 20, wherein the total time the eye contact devices engage said corneas is less than about five seconds.

25. A method as claimed in claim 24, wherein the total time the eye contact devices engage said corneas is about three seconds.

26. A method as claimed in claim 20, wherein said characteristics include amplitudes and areas of the waveshapes derived from each eye, the amounts of distortion of the waveshapes derived from each eye, and the delay time of the waveshapes from each eye with respect to the corresponding ECG signal, wherein said amplitudes, areas, distortion and delay time serve to permit said inference.

27. Apparatus for noninvasively sensing ocular pulses of a mammal, which pulses serve as a basis for indicating presence of a disease or malfunctioning body part which causes alterations in the ocular pulses, that comprises:

piezoelectric transducer means to receive simultaneously undamped ocular pulses from the two eyes of the mammal and operable to convert the ocular pulses to signals in the form of similar complex electric pulses whose individual shape corresponds identically to the corresponding shape of the undamped ocular pulses, said transducer means comprising a pair of simultaneously operative piezoelectric benders disposed to bend by substantially horizontal movement, having eye contact elements positioned to engage simultaneously the respective corneas of the two eyes disposed substantially vertically and having support means supporting said piezoelectric benders for movement of said eye contact elements substantially horizontally into engagement with the respective corneas; and means connected to receive said signals and operable to permit derivation of information from which the presence of a disease or malfunctioning body part can be inferred.

28. Apparatus as claimed in claim 27, wherein the piezoelectric transducer means is also operative to produce signals corresponding to the intraocular pulse in both eyes simultaneously.

29. Apparatus as defined by claim 27, in which the disease or malfunctioning body part is a condition of glaucoma of said at least one eye, in which said means connected comprises display means operable to display said signals as a series of waveshapes, and in which said information is found in the shape of each waveshape, in said series of waveshapes.

30. Apparatus for noninvasively sensing ocular pulsations of a mammal, which pulsations serve as a basis for indicating presence of a disease or malfunctioning body part which causes alterations in the ocular pulses, said pulsations being complex waveforms that include, in the healthy mammal, a dicrotic notch, that comprises:

piezoelectric transducer means to receive simultaneously undamped ocular pulsations from the two eyes of the mammal and operable to convert the ocular pulsations to signals in the form of similar complex electric pulses whose individual shape corresponds identically to the corresponding shape of the ocular pulsations and including said dicrotic notch, said transducer means comprising a pair of simultaneously operative piezoelectric benders disposed to bend by substantially horizontal movement, having eye contact elements positioned to engage simultaneously the respective corneas of the two eyes disposed substantially vertically and having support means supporting said piezoelectric benders for movement of said eye contact elements substantially horizontally into engagement with the respective corneas; and means connected to receive said signals and operable to permit derivation of information from which the presence of a disease or malfunctioning body part can be inferred.

31. Apparatus as claimed in claim 30, wherein the piezoelectric transducer means is also operative to produce signals corresponding to the intraocular pulse in both eyes simultaneously.

32. Apparatus according to claim 30 in which the lasted-named means is operable to permit determination of peak-to-peak value of the dicrotic notch, area under the individual waveform, the anacrotic slope of the individual waveform and the catacrotic slope of the individual waveform.

* * * * *